United States Patent [19]

Horiuchi

[11] Patent Number: 4,643,174
[45] Date of Patent: Feb. 17, 1987

[54] ADJUSTABLE CERVICAL SPINE CORSET AND TRUCK CORSET

[76] Inventor: Tohru Horiuchi, 2-1-1 Shintomi-cho, Tomakomai-shi, Hokkaido, Japan

[21] Appl. No.: 620,830

[22] Filed: Jun. 15, 1984

[30] Foreign Application Priority Data

Oct. 1, 1983 [JP] Japan .................. 58-184266
Oct. 1, 1983 [JP] Japan .................. 58-184267
Oct. 1, 1983 [JP] Japan .................. 58-184268

[51] Int. Cl.⁴ ............................................. A61F 5/08
[52] U.S. Cl. .................... 128/76 R; 128/75; 128/87 B
[58] Field of Search ............... 128/87 R, 87 A, 87 B, 128/87 C, 75, 76 R, DIG. 19, DIG. 23

[56] References Cited

U.S. PATENT DOCUMENTS

| D. 198,069 | 4/1964 | Connelly | 128/75 |
| D. 248,872 | 8/1978 | Thomas | 128/75 |
| 2,904,040 | 9/1959 | Hale | 128/87 R |
| 3,224,439 | 12/1965 | Blair, Jr. | 128/75 |
| 3,507,273 | 4/1970 | Yellin | 128/87 R |
| 3,601,123 | 8/1971 | McFarland | 128/75 |
| 3,724,452 | 4/1973 | Nitschke | 128/75 |
| 3,957,040 | 5/1976 | Calabrese | 128/75 |
| 4,219,193 | 8/1980 | Newman | 128/76 R |
| 4,383,523 | 5/1983 | Schurman | 128/75 |
| 4,385,627 | 5/1983 | Nelson | 128/76 R |

FOREIGN PATENT DOCUMENTS

| 227677 | 2/1960 | Australia | 128/75 |
| 2259863 | 6/1974 | Fed. Rep. of Germany | 128/75 |
| 873138 | 7/1961 | United Kingdom | 128/75 |
| 1015207 | 12/1965 | United Kingdom | |
| 1466222 | 3/1977 | United Kingdom | |

Primary Examiner—Gene Mancene
Assistant Examiner—J. R. Hakomaki
Attorney, Agent, or Firm—Oblon, Fisher, Spivak, McClelland, & Maier

[57] ABSTRACT

A back support frame made of a bendable metal wire and having an occiput rest at the top end is detachably mounted about at the center of a back plate and extended upwardly therefrom. A shoulder support frame is attached about at the center of the back support frame and extended therefrom so as to surround the front part of a patient's body. A chest plate is detachably mounted to the lower end of the shoulder support frame. A pair of cheek rest frames are secured about at the center of the shoulder support frame and extended forward orthogonally. Belts are attached at lower left and right ends of the back plate, which are put by way of the armpits around the chest of the patient and detachably secured at their ends to the chest plate.

A trunk corset dividable into a cervical spine part, a thoracic spine part, and a lumbar spine part can be assembled so that they are adjustable and rapidly detachable. The relative position between the back part and the lumbar part can be adjusted in accordance with the sitting height of a patient. A pair of cheek rests in contact with both cheeks of the patient to support them are mounted at the upper ends of the cervical spine part. A sufficient degree of freedom to allows the patient to speak and eat meals.

10 Claims, 29 Drawing Figures

ADJUSTABLE CERVICAL SPINE CORSET AND TRUCK CORSET

FIELD OF THE INVENTION

This invention concerns a cervical spine corset capable of adjusting the fixing force to the cervical spine as desired. More specifically, it relates to a wire metal type cervical spine corset of a simple structure comprising, in combination, villi type tape fasteners instance, Velcro fasteners (trademark) and bendable metal members instance, metal wires), as well as to a metal wire type cervical spine corset and a separatable type trunk corset further comprising additional portions put to the back and the chest of a patient for obtaining more reliable and adjustable clamping force.

BACKGROUND OF THE INVENTION

Heretofore, various trunk supporting devices or trunk corsets have been used with an aim of external fixation to cervical spines. Fixing collars for cervical spine are effective for the therapy of patients suffering from structural lesions of cervical spines. However, since the necessary fixing force is different depending on the degree of lesion of patients, a fixing device once selected has often been obliged to be replaced with another depending on the case to result in economical disadvantage, although the fixing force of the individual device can be adjusted to some extent.

Further, while the supporting performance for jaw and occipital nodes has so far been considered most important upon fixing the cervical spine, it has been found that the supporting force is not required so much depending on the type and degree of symptoms.

On the contrary, fixation that has been applied particularly from below the lower jaw not only results in inconveniency in ordinary diet and conversation, but also gives physical stimulations to focus region by way of a lever-like route having a fulcrum at the lower jaw when eating and talking which may rather worsen the symptoms and also give undesired psychological effects as well.

Further, support for the occipital nodes may result in sensation to a patient's occiput in relation with a pillow, thereby hindering the sound sleep.

Furthermore, the conventional supporting devices include many parts in close contact with the periphery of the cervical spine. This can cause uncomfortable feelings and troubles such as feelings of fever or sweating, particularly, in the summer seasons. Moreover, they provide drawbacks also in other sanitary points of view.

ADVANTAGES OF THE INVENTION

Cervical spine corsets according to this invention, when fitted to many patients, can restrict all of the movements including forward flexion, backward flexion, lateral flexions and rotation of the cervical spine. Accordingly they can attain the same purpose as that of the conventional fixing collars. Furthermore, the present corset is light in weight, easy to handle with and gives no troubles in the diet or conversation since a patient can open his mouth freely even when he is put within the corset. Furthermore, according to particular preferred embodiments of this invention, since there is less area in close contact with patient's skins, it provides better ventilation and releases the patient from feelings of fever and sweating, particularly in the summer season, thus giving no uncomfortable feelings during use and performing excellent effects also in the sanitary points of view.

According to this invention, it is no longer necessary to design the individual shape of the cervical spine corset on every patient. If a corset is prepared with the size of a certain range, it can be adjusted in accordance with the body constitutions of patients and can be used repeatedly.

Further, since the fixing force can be adjusted depending on the symptoms of a patient, it can be used continuously till he is completely cured without requiring to be replaced with other corsets. Furthermore, since neither the lower jaw nor the occipital node is fixed, the patient can freely take ordinary diet and make conversation at will. Thus it can provide good effects in psychological point of views as well.

In addition, since the occipital node is not supported, it gives no uncomfortable sensation to the occiput in relation with the pillow during sleep, whereby the patient can sleep well.

Explanation will further be made for the remarkable feature of this invention against structural lesions of the cervical spine, for instance, whiplash injury and lumbar distorsion combined therewith.

Conventional theraputical trunk corsets for use in the rest of spines, particularly, cervical spines are adapted such that a neck part, a chest part and a lumbar part are clamped by an integral cylindrical structure as shown, for instance, in Current Trend of Orthotics in the United State of America, described in Pacific News, by Siegfried W. Paul C.P.O. Accordingly, even if a patient wants to remove, for instance, the lumbar spine part or thoracic spine part for which fixation is no more necessary depending on the degree of recovery and the use of purpose, it has been impossible in the conventional trunk corsets.

For instance, in the case of cervical lesions, it is impossible to use a corset while separating only the cervical spine fixing part from the corset and, on the contrary, it is neither possible to improve the fixing force by restoring such a part. Furthermore, it has been impossible, particularly for the case of a child, to extend or compress the longitudinal axis of the corset adjustably depending on the growth of the body.

This invention has been made in order to overcome the foregoing drawbacks and it provides a trunk corset capable of varying the relative position and the fixing force of a thoracic spine part, a lumbar spine part and a cervical spine part optionally even during the use of the corset, and separating or attaching particular parts from below to decrease or increase the fixing force and thereby to improve the therapeutic effects.

BRIEF SUMMARY OF THE INVENTION

In summary, the cervical spine corset of this invention can be obtained by constituting a jaw rest and an upper chest contact part with wire metals, and adjustably connecting the connection points between them and a posterior neck rest by means of villi type fasteners.

Another embodiment of this invention can be obtained by securing a back part at the rear end of a wide main body mounted on both shoulders of a patient, attaching an adjustable chest part to the front end of the main body, adjustably and detachably mounting on occiput rest to the rear portion thereof and a cheek rest to a front portion of the main body, and adjustably connecting the back part and the chest part by means of belts having villi type fasteners passing under the armpits of the patient.

A still another embodiment of this invention can be constituted by separately preparing a chest part, a back part, an occiput rest, cheek rests, etc. and adjustably connecting them with belts having villi type fasteners.

In a particular embodiment of this invention, the trunk corset comprises preferably a thoracic spine part of front chest part and back part, a lumbar spine part and a cervical spine part made of synthetic resin material and metal material respectively. The lumbar spine part has generally an annular shape in section so as to cover a patient's lumbar part, which has an opening at its front upon use, and the discontinuous front portion is closed and fastened by means of belts such as villi type fastener, such as Velcro tapes. At the back of the lumbar part, are secured a lumbar support beam corresponding to a patient's spinal column and sub-support beams for reinforcing the fixing force on both sides thereof. A metal support strip plate is secured at the back part and sets of shoulder belts and lumbar belts are attached respectively to the upper and lower side ends. On both sides of the metal support strip plate are disposed receptacle metals for inserting therein to support the respective ends of the sub-support beams. The lumbar support beam is adjustably secured by screws to the metal support strip plate. Similarly, a support beam for a temple—occiput rest is screwed adjustably, that is, slidably on the upper part of the lumbar support. The cervical spine part is detachably mounted to the thoracic spine part and the cervical spine part has, on its extension, fences for supporting both cheeks of a patient therebetween. Thus, the patient fitted with the present trunk corset is prevented from the mobility for his body, neck and head. Each of the foregoing parts can be selected and assembled optionally depending on the degree of lesions and the recovery of the patient.

Accordingly, it is the first object of this invention to provide a cervical spine corset comprising a jaw fixing part and a part in contact with the upper chest of a patient each made of wire metals, and a posterior neck rest connected adjustably to them by using villi type fasteners.

The second object of this invention is to provide a cervical spine corset comprising a wide main body to be carried on patient's shoulders and cheek rests and an occiput rest mounted adjustably by means of wire metals respectively to the front and rear portions thereof.

The third object of this invention is to provide a cervical spine corset comprising a thoracic spine part, a back part, an occiput rest and a cheek rest adjustably connected by means of bendable wire metals and villi type fasteners.

The fourth object of this invention is to provide a separable trunk corset comprising a thoracic spine part, a lumbar spine part and a cervical spine part, the relative position and the clamping force or fixing force of which can freely be adjusted even in the use of the corset and which can be detached from the lower parts of the parts.

DETAILED DESCRIPTION OF THE PREFERRED EMBODIMENTS

This invention will now be explained referring to preferred embodiments thereof in conjunction with the accompanying drawings. At first, the method of manufacturing the first embodiment is to be described for the aid of understanding the structure and the constitution thereof.

As shown in FIG. 1 through FIG. 6, the first embodiment is manufactured as described below. A frame is prepared from a metal wire 1, for example, of 5 mm in diameter that can be bent adjustably as required and has a recovering resiliency, by bending the wire 1 into a U-shaped configuration, up-turning both U-leg parts, bending the leg tops respectively into a U-shape of an elevational view to form belt attaching parts 2 and then further bending the top ends 3 downwardly. A reinforcing member 4 is attached at the front part of the frame.

Figure 1:
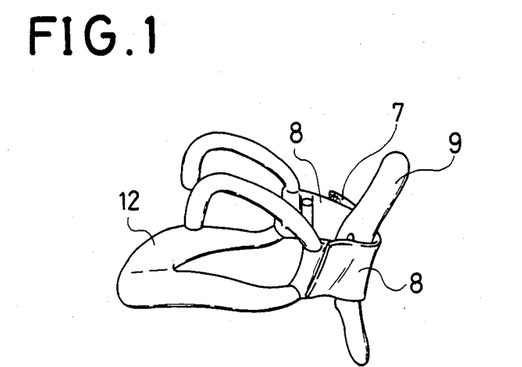
FIG. 1 is a perspective view for the first embodiment of this invention.
Figure 2:
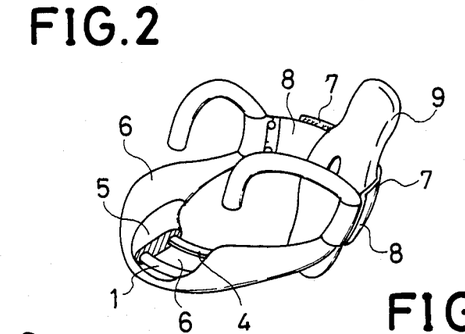
FIG. 2 is a partially cut away perspective view for the first embodiment illustrating the inner structure of a frame.

The entire circumference of the frame is covered with a rigid sponge material 5 and further covered thereover with shock absorber material 6 such as urethane rubber.

Detachable belts 8 respectively are attached to the belt attaching parts 2 with villi type tapes 7.

Belts fixtures 10 are secured to an occiput rest 9 so as to be held vertically. After passing the belts 8 through the respective belt fixtures 10, they are turned back and fixed by the villi type tapes 7.

In the use of the corset according to this invention having the foregoing structure, one of the belts 8 of the cervical spine corset is at first detached from the belt fixture 10, and then the U-shaped frame is spreaded at its opening by both hands and inserted from the anterior part of a patient's neck and secured therearound. The curvature of the frame is adjusted so as to apply an adequate fixing force for restricting the movement of the cervical spine. While abutting the occiput rest 9 against the occipital portion of the patient, the belt 8 is passed through the belt fixture 10, turned back and then fastened by the villi type tape 7. The position for the occiput rest 9 can easily be adjusted finely by loosening and tightening the belt 8 (refer to FIGS. 4, 5 and 6).

Since a metal wire that can be bent adjustably and has a recovering resiliency is used as the metal wire 1 in this invention, the fixing force can optionally be varied. Accordingly, the fixing force of the corset can be weakened in accordance with the degree of lesion of a patient, since less fixing force is necessary as the symptoms of the patient are relieved.

Figure 3:
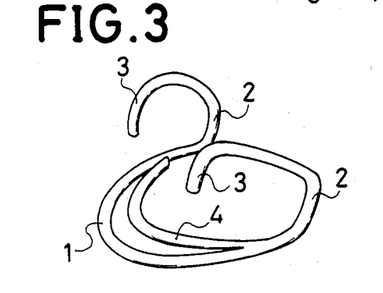
FIG. 3 is a perspective view for the frame.
Figure 4:
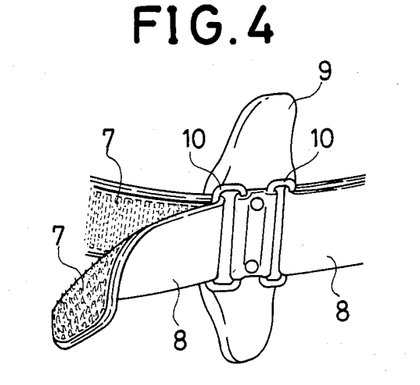
FIG. 4 is a perspective view illustrating the attachment of an occiput rest in the first embodiment.
Figure 5:
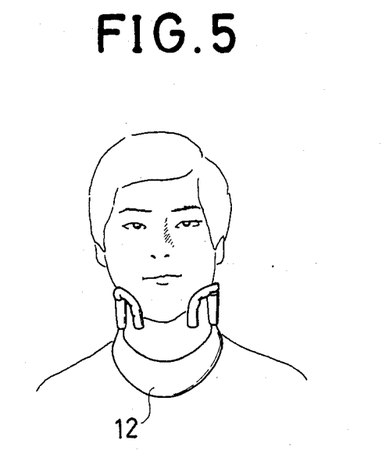
FIG. 5 is a front elevational view illustrating the method of using the cervical spine corset of the first embodiment.
Figure 6:
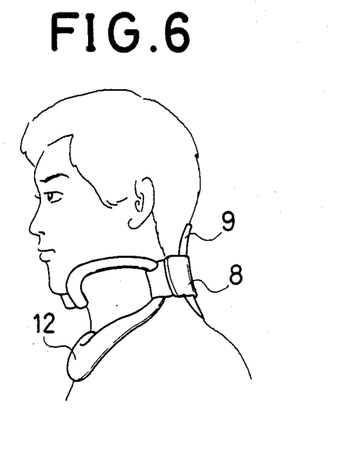
FIG. 6 is a side elevational view of the corset shown in FIG. 5.

As shown in FIG. 3, the U-shaped reinforcing member 4 is disposed to the inside of the frame, whereby the rigid sponge material 5 covering the entire circumference of the frame can be set steadily and the strength of the frame itself is also improved.

Figure 7:
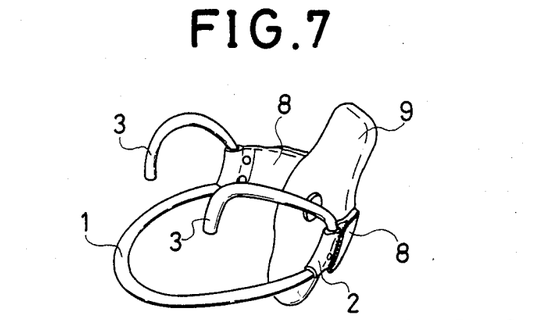
FIG. 7 is a perspective view for the second embodiment of this invention using single part of wire.

FIG. 7 shows a second embodiment of the cervical spine corset according to this invention, in which belts 8 and an occiput rest 9 are directly attached to a frame of metal wires 1, 2, 3.

Figure 8:
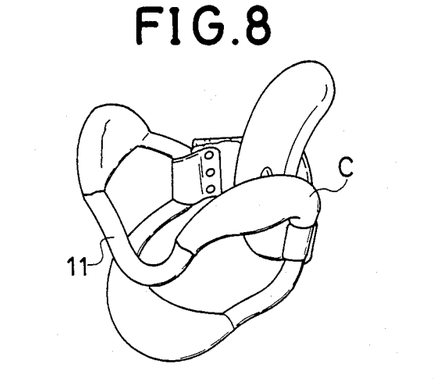
FIG. 8 and FIG. 9 are perspective view and side elevational view respectively for the third embodiment of this invention.
Figure 9:
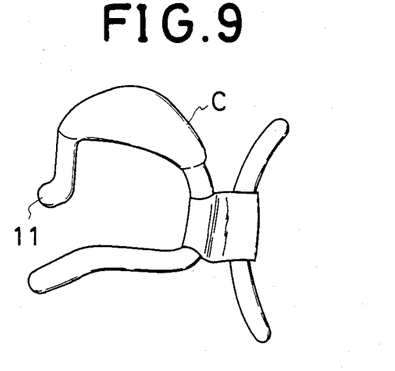

FIG. 8 and FIG. 9 show a third embodiment according to this invention, in which a connection 11 is disposed between both top ends of a frame for the cervical spine corset to integrate the same, which is covered with rigid sponge material and shock absorber material. Rigid sponge material is incorporated into a portion in contact with the patient's cheeks.

Figure 10:
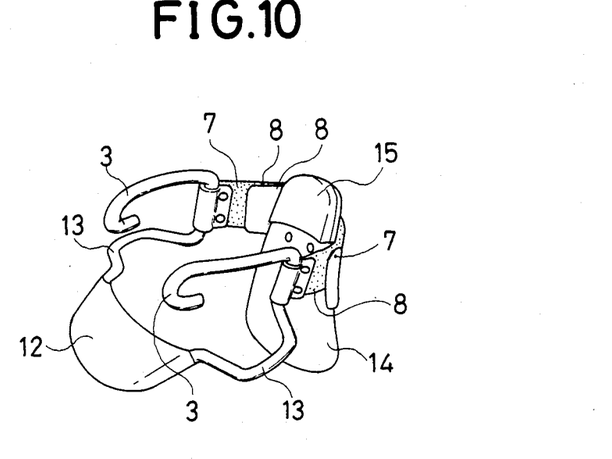
FIG. 10 is a perspective view for the fourth embodiment of this invention.

FIG. 10 shows a fourth embodiment according to this invention, in which rigid sponge material is applied over the entire circumference of a frame and shock absorbing material is further covered thereover. Each top end 3 of the frame is bent downwardly in a hook-shape, and a thoracic rest 12 is formed on the front part of the frame, so that the entire frame can be received stably on the thoracic bone. Further, the frame is extended outwardly on both sides thereof to form a clavicula rest 13, so that the frame is more stably received on the patient's clavicula.

As shown in FIG. 10, a thoracic spine rest 14 made of synthetic resin is formed in a shape like that of a shoehorn and appended at the upper inside thereof with sponge material 15 and at the upper outside thereof with a villi type tape 7. A tape 7 is attached to the inside and the outside of one belt 8 and another similar tape 7 is also appended to the inside of the other belt 8.

Figures 11, 12:
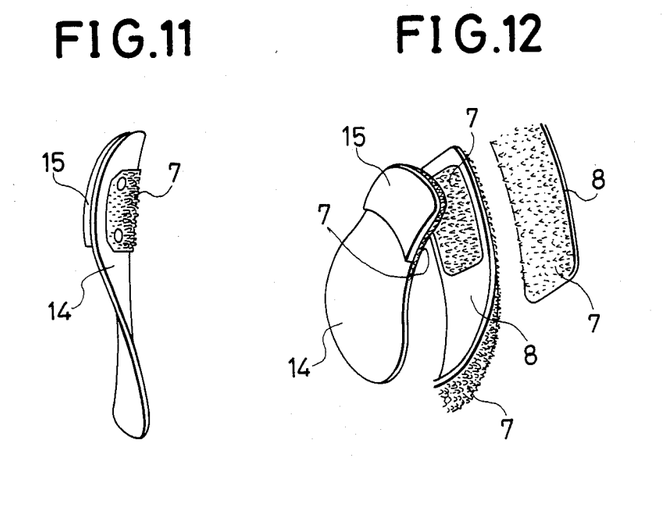
FIG. 11 is a side elevational view for a thoracic spine rest adapted to be used in the fourth embodiment.
FIG. 12 is a perspective view illustrating the method of attaching the thoracic spine rest shown in FIG. 11 and that of fastening Velcro tapes.

On fitting the cervical spine corset to a patient who requires the external fixation for his cervical spine, the curvature of the frame is adjusted so as to apply a sufficient fixing force to restrict the movement of the cervical spine, the frame is spreaded at its opening by both hands and inserted from the anterior part of the patient's neck. Then, as shown in FIG. 12, while abutting the thoracic spine rest 14 against the posterior portion of the neck, a belt 8 having tapes 7 appended on its both surfaces is attached, whereby the tape 7 on the thoracic spine rest 14 and the tape 7 on the belt 8 are engaged fixedly to each other. By covering or applying the tape 7 of one belt 8 over the tape 7 of the other belt 8, the thoracic spine rest 14 is firmly fixed at the posterior portion of the neck and received on the thoracic spine. Then, all of the movements including forward flexion, backward flexion, lateral flexion and rotation of the cervical spine are restricted.

Referring then to a fifth embodiment shown in FIGS. 13 through 18, a main body 21 is formed in a U-shaped configuration and curved so as to conform to the shoulders of a patient. The main body 21 is attached at its inside with shock absorber material 22 made of rigid sponge or the like.

Figure 13:
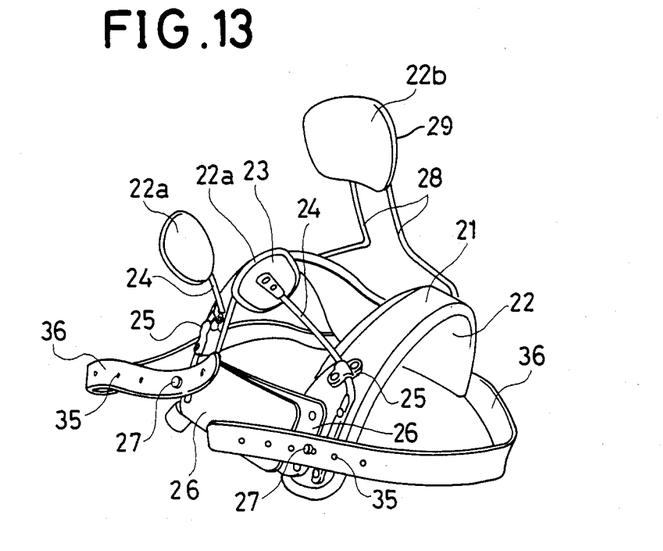
FIG. 13 is a perspective view for the fifth embodiment of this invention.
Figure 14:
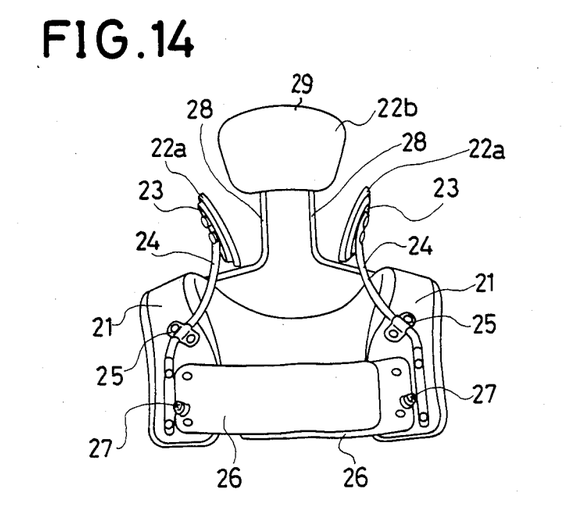
FIG. 14 is a front elevational view for the fifth embodiment with some members being partially removed.

Shock absorber material 22a is attached to the inside of each cheek rest 23. A pair of support frames 24 that can be bent adjustably and have recovering resiliency are fixed to the outside of the cheek rests 23, 23. The support frames 24 are secured to both front sides of the main body 21 respectively by means of metal fixtures 25, rivet calking or the like.

A chest plate 26 provided with appropriate engaging means such as made of villi type tape (not shown) is secured to both front sides of the main body 21.

Belt engaging pins 27 are planted on both front sides of the main body 21.

An occiput rest 29 is mounted at the upper portion of a support frame 28 usually at a height slightly lower than the occipital node of a patient, with a slight clearance or gap to a metal fixture 25 fixed on the back portion of the main body so that the mounting angle can be varied desirably.

The support frame 28 is secured at the back of the main body 21 by means of metal fixtures 25, rivet calking or the like.

Figure 15:
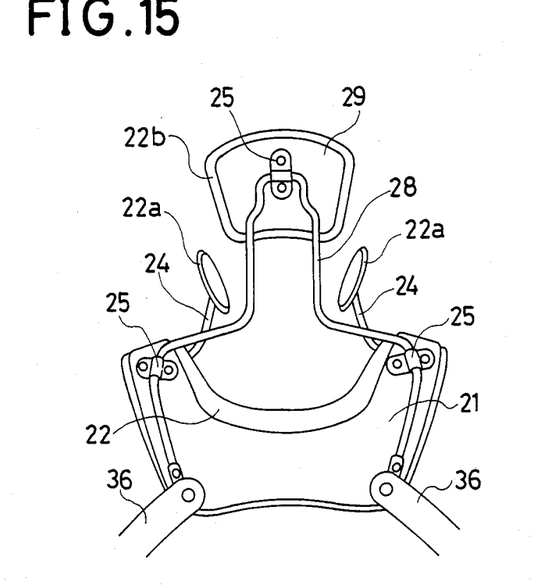
FIG. 15 is a back elevational view for the fifth embodiment shown in FIG. 14.
Figure 16:
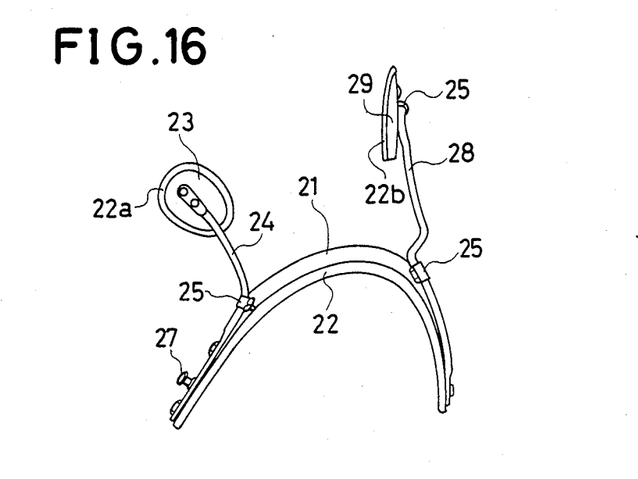
FIG. 16 is a left-hand side elevational view for the fifth embodiment.

Belts 36 each perforated with a plurality of apertures 35 are attached respectively to both lower ends at the back of the main body 21.

Figure 17:
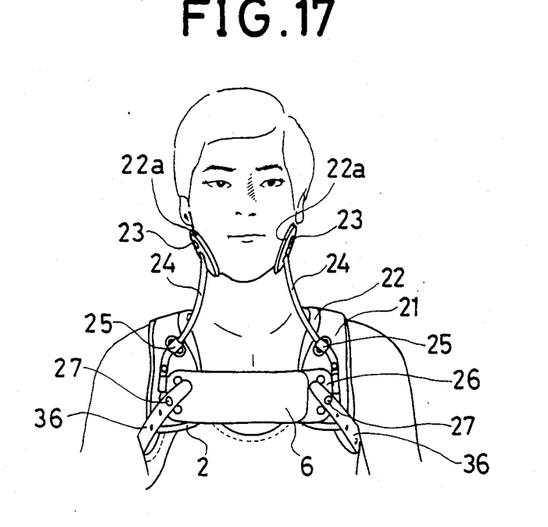
FIG. 17 is a front elevational view illustrating the method of using the fifth embodiment.

Upon using the embodiment according to this invention having the foregoing structure, the main body 21 of the cervical spine corset is fitting from behind to a patient who requires external fixation for the cervical spine, by spreading the main body 21 at its front opening by both hands, placing the curved interior surface on both shoulders and engaging the chest plate 26 with tapes or the likes not illustrated. The belts 36 are passed under both armpits, and each of the belt engaging pins 27 is inserted into a suitable aperture 35 that can provide an appropriate clamping. The occiput rest 29 is usually situated at a position lower than the patient's occipital node so that the occiput rest 29 does not support the occipital node. The height of the occiput rest is about the same as in the case of a conventional fixing collar: "POLYNECK" (trade name).

The curvature of the support frame 24 is adjusted so as to obtain an appropriate fixing force by the cheek rests 23 to the patient's cheeks.

Figure 18:
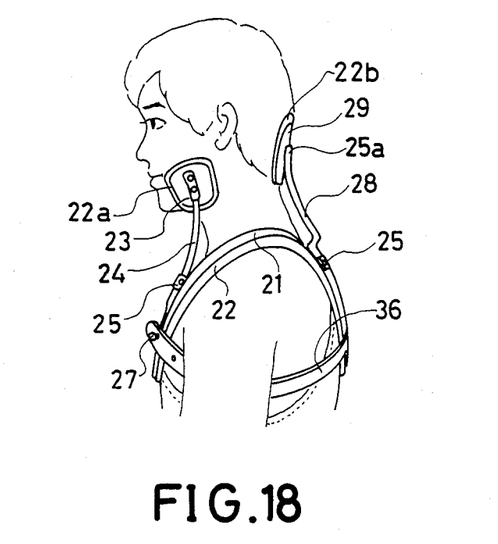
FIG. 18 is a left-hand side elevational view illustrating the method of using the fifth embodiment shown in FIG. 17.

FIG. 17 and FIG. 18 show the state of fitting the cervical spine corset to a patient, in which all of the movements of the cervical spine are restricted by the cheek rests 23 and the occiput rest 29.

Since the main body 21 is made of a thin stainless steel sheet or synthetic resin and the support frames 24, 28 are made of materials that can be bent adjustably and have recovering resiliency (for example, an aluminum rod in the embodiment according to this invention), the fixing force can optionally be varied by merely bending to adjust the frames with hands. Thus, the fixing force can be weakened in accordance with the degree of lesions of the patient since less fixing force is necessary as the symptoms of the patient are relieved.

The structure of a sixth embodiment according to this invention will be explained next referring to FIG. 19 through FIG. 27.

Figure 19:
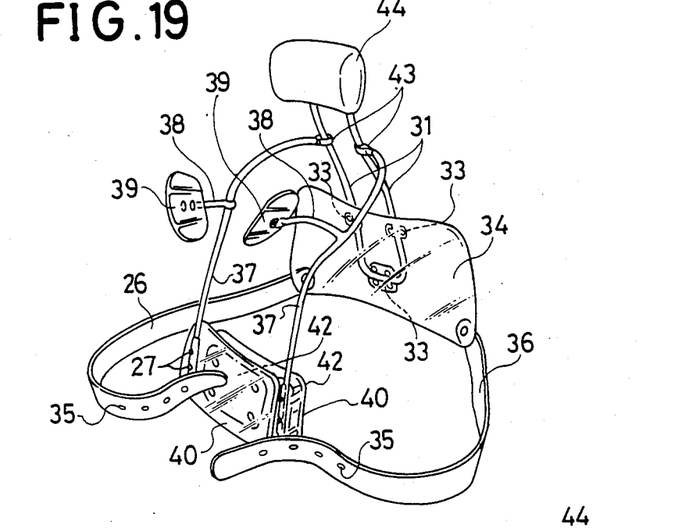
FIG. 19 is a perspective view for the sixth embodiment of this invention.

At an upper portion of a circular back support frame 31 is mounted an occiput rest 32 usually at a height lower than the occipital node of a patient by metal fixtures 33, 33 with an appropriate gap so that the mounting angle can optionally be varied.

A back plate 34 is secured at the lower portion of the back support frame 31 by means of a metal fixture 33. Belts 36 each perforated with a plurality of apertures 35 are disposed at both lower ends of the back plate 34.

A pair of cheek rest support frames 38 that can be adjustably bent and have recovering resiliency are symmetrically attached to an appropriate position of a support frame 37 and cheek rests 39 are respectively attached to the upper inside portions of the support frames 38.

Belt engaging pins 27 are mounted on a chest plate 40 at the lower end, and tapes 42 are appended at the rear face of one chest plate 40 and at the front surface of the other chest plate 40.

The support frames 37 are secured to the chest plate 40. The support frames 37 are also joined at appropriate upper portion of the back plate support frame 31 by means of connecting metal fixtures 43 such that the support frame 37 does not move vertically on the back support frame 31, but can be rotated rightwardly and leftwardly.

A cover 44 is attached to the occiput rest 32 so as to provide a comfortable feeling of contact to the patient.

When using the sixth embodiment having the foregoing structure, a pair of the support frames 37 of the cervical spine corset are opened outwardly with the connecting metal fixtures 43 of the swinging centers by both hands, and the support frames 37 are engaged to each other from behind to the neck of a patient who requires fixation for the cervical spine. The chest plates 40 are then engaged to each other by fastener tapes 42. The clamping force between the chest plates 40 can also be adjusted simply. The belts 36 are passed under both of the armpits respectively and the belt engaging pins 27 are inserted respectively, into the apertures 36 that can provide an appropriate clamping force.

The curvature for each of the check rest support frames 38 is adjusted so that the cheek rests 39 provide an appropriate fixing force to the patient's cheeks. The occiput rest 32 is usually situated at a height lower than the occipital node of the patient in order that the rest 32 does not contact with and support the occipital node. The height of the rest 32 is about the same as that in the conventional fixing collar "POLYNECK (Trademark)".

Figures 24, 25, 26, 27:
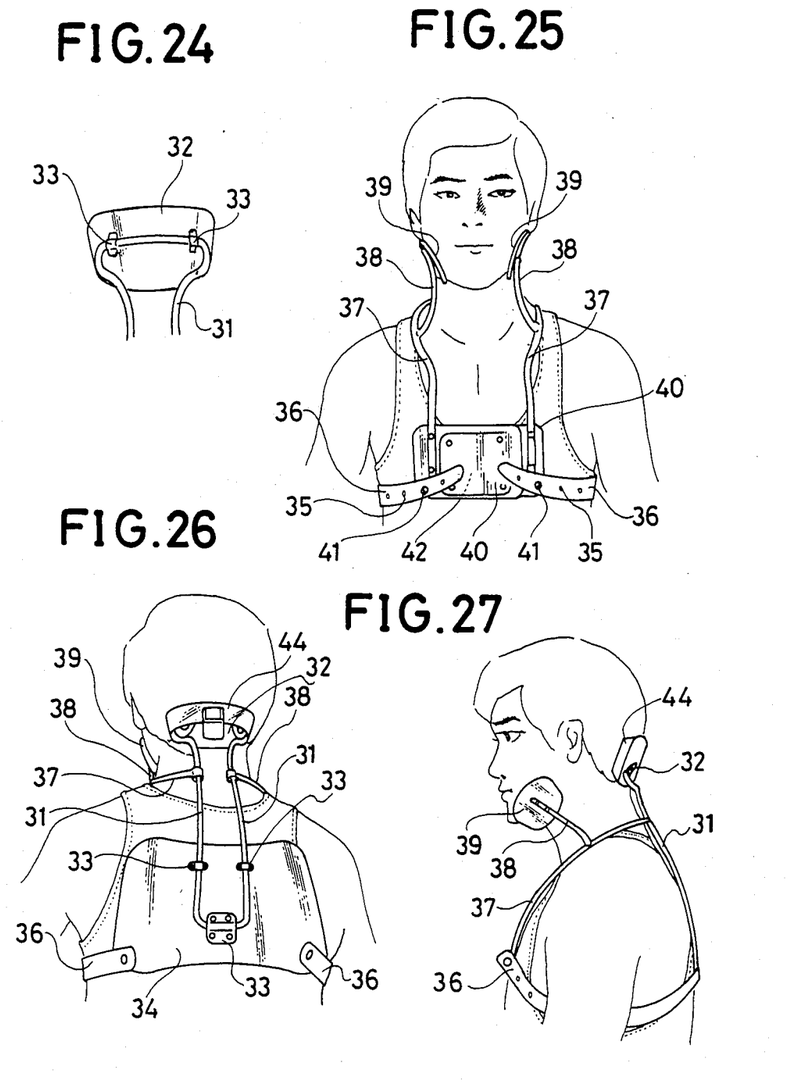
FIG. 24 is a back elevational view illustrating the attachment of an occiput rest.
FIG. 25 is a front elevational view showing the method of using the sixth embodiment.
FIG. 26 is a back elevational view for the sixth embodiment shown in FIG. 25.
FIG. 27 is a side elevational view for the sixth embodiment shown in FIG. 25.

FIG. 25 is a front elevational view illustrating the state of wearing the cervical spine corset according to this invention, FIG. 26 is a perspective view illustrating that state from behind, and FIG. 27 is a side elevational view thereof. It will be noted that the forward flexion, backward flexion, lateral flexions and rotation of the cervical spine of the patient are restricted by the cheek rests 39 and the occiput rest 32.

Figure 20:
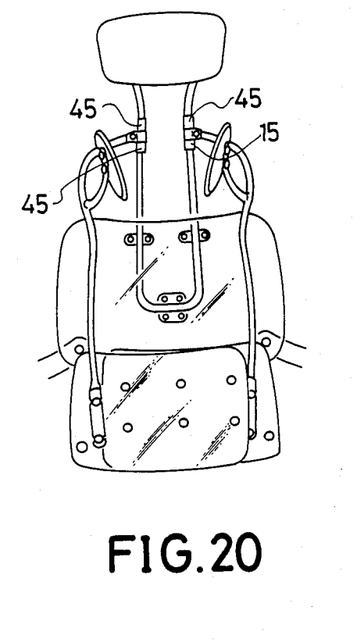
FIG. 20 is a perspective view for the sixth embodiment in FIG. 19, viewed in front of it from above.
Figure 21:
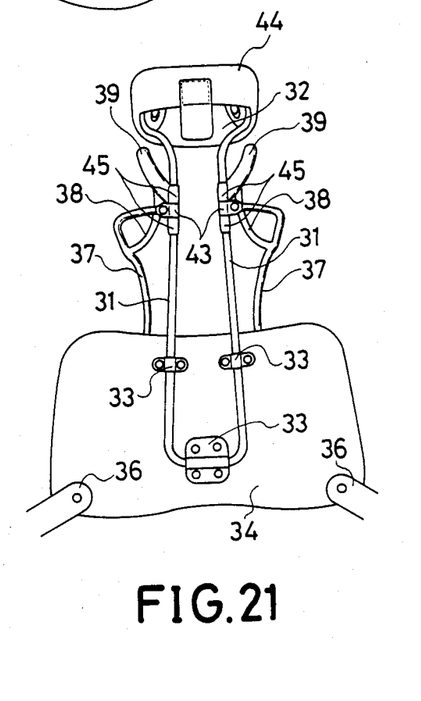
FIG. 21 is a back elevational view for the sixth embodiment.
Figure 22:
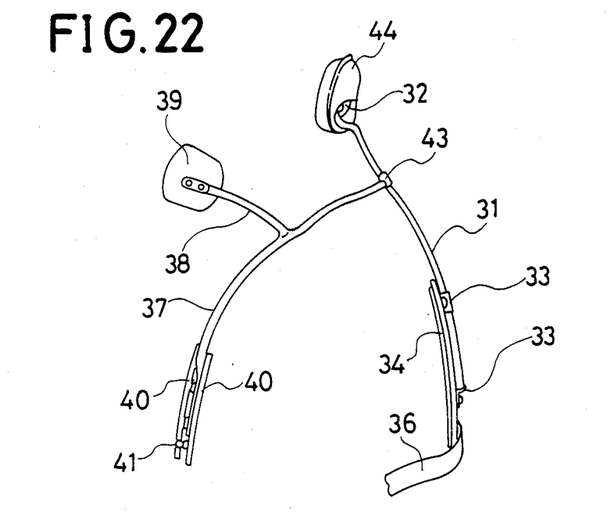
FIG. 22 is a left-hand side elevational view for the sixth embodiment.

The connection between the back support frames 31 and the support frames 37 are arranged such that the support frames 37 do not move vertically on and along the back support frames 31, but can be rotated rightwardly and leftwardly. For instance, as shown in FIG. 20 and FIG. 21, each frame 31 is crushed above and below the portion where the connecting metal fixture 43 is attached to form pressed and spread portions 45, 45 having radial stops so that the connecting metal fixture 43 may not displace vertically.

Hindrance of the vertical movement of the support frame 37 can also be attained by compressing or squeezing only the portions of the frame attached with the connecting metal fixture 43 over the entire circumference to reduce the diameter thereof smaller than that for the back support frame 31 and mounting the connecting metal fixture 43 thereto.

The cheek rests 39, the back plate 34, the chest plate 40 and the occiput rest 32 are made of synthetic resin in this embodiment. In the case where a fashionable corset is desired, these members may be made of transparent synthetic resin.

Figure 23:
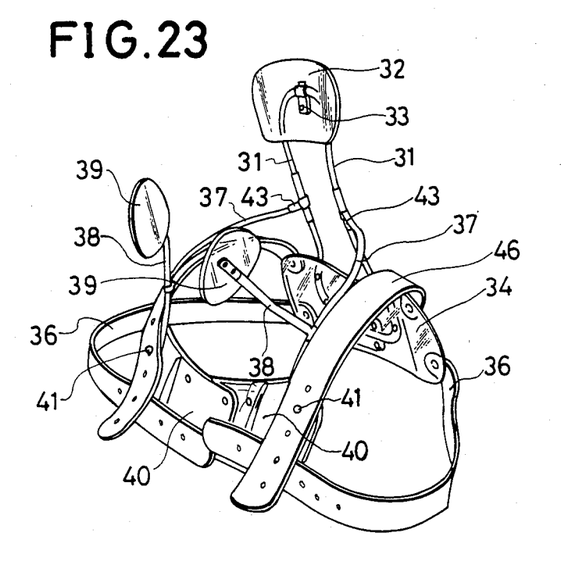
FIG. 23 is a perspective view for the sixth embodiment, showing a particular case in which shoulder belts are attached to the cervical spine corset.

In the embodiment shown in FIG. 23, shoulder belts 46 are additionally mounted to both upper ends of the back plate 34 in the cervical spine corset. Belt engaging pins 41 are mounted respectively at the projected upper ends of the chest plates 40, on which pins the belts on both shoulders are engaged.

It will be apparent from the foregoing explanation that each of the first through sixth embodiments according to this invention basically comprises a jaw rest, a thoracic bone rest, a back rest and an occiput rest as main constituent members which are represented here by the terms of "check rest", "chest plate", "spine fixture", "cervical rest" or the like depending on the difference in the positions in which they are applied and in the manner in which they are constituted.

Figure 28:
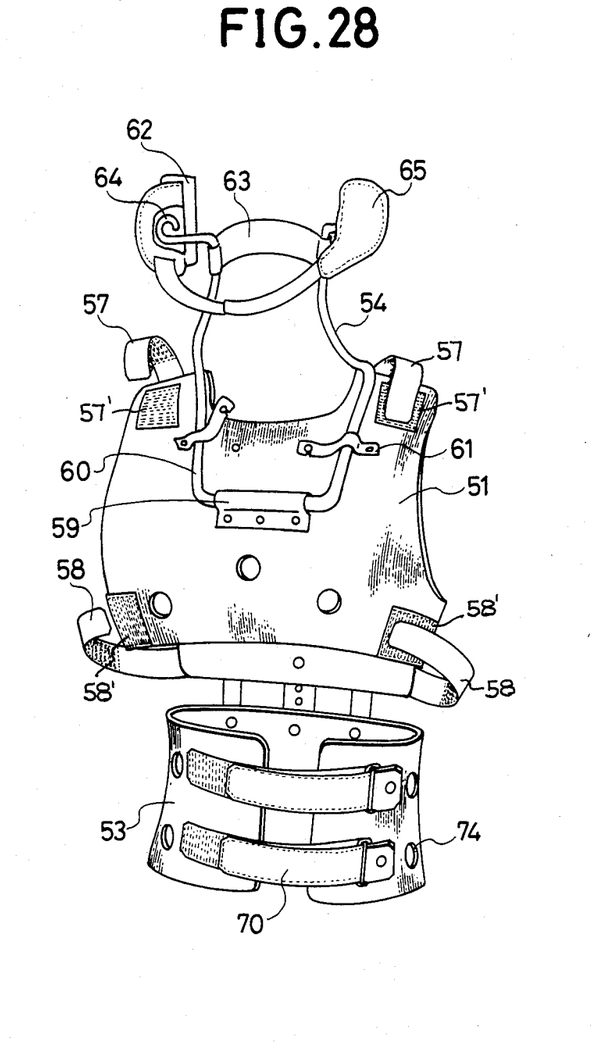
FIG. 28 is a perspective view illustrating a chest part, a cervical spine part and a lumbar spine part of a separable type trunk corset according to the seventh embodiment of this invention.
Figure 29:
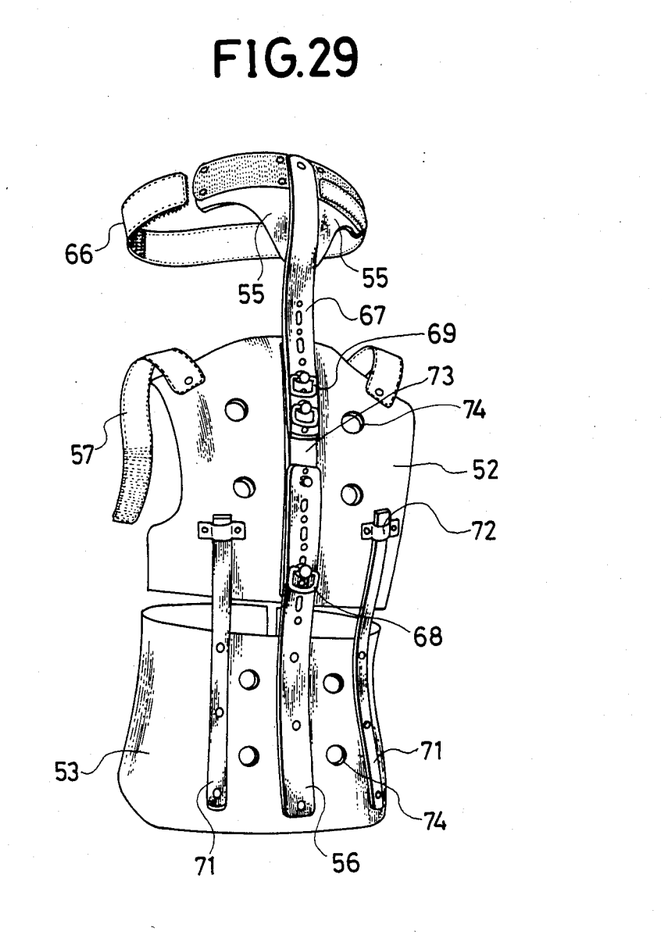
FIG. 29 is a perspective view showing, from behind, the separatable type trunk corset comprising a back part, a temporal—occipital region rest and the lumbar spine part attached thereto.

Then, a seventh embodiment according to this invention will be described in conjunction with FIG. 28 and FIG. 29. As shown in the drawings, the trunk corset according to this invention is usually assembled from a chest part 51, a back part 52, a lumbar spine part 53 and a cervical spine part 54 as main constituent elements and applied to a patient. The chest part 51 and the back part 52 are combined to constitute a thoracic spine part of the trunk corset. The relative position between the back part 52 and the lumbar spine part 53 is determined by securing a lumbar support beam 56 at its lower portion to the lumbar spine part 53 (for example, by rivetting). The upper portion of the lumbar support beam 56 is secured by threading engagement to a metal support plate 73 which is secured to the surface of the back part 52. The thoracic spine or chest part 51, the back part 52 and the lumbar spine part 53 are respectively made of synthetic resin material. The lumbar support beam 56 and the metal support plate 73 are preferably made of metal material non-deleterious to a human body and having such a rigidity as can be adjusted for the curvature (for instance, stainless steel).

A cervical spine part 54 to be attached to the upper portion of the thus fixed thoracic spine part 51 is mostly composed of a fine strip of a stainless steel or a plated metal wire of a somewhat larger diameter and bended generally in an L-shaped configuration when viewed from the lateral side. The upper top ends of the cervical spine part 54 which are to be abutted against both cheeks of a patient upon use are respectively bent circularly. Cheek rests 65 made of soft plastics are mounted on the upper top ends of the cervical spine part 54. FIG. 28 shows the cheek rest 65 partially cut away to illustrate the bent portion. The cheek rest 65 at the left is shown in the state before use rotated forward by 90 degree.

The cheek rest 65 comprises a set of left and right parts which are connected to each other in front of patient's mouth by means of a leather belt or a villi type belt attached to the end of each part. By the use of the cheek rest, the fixing force for the cervical spine can be increased further, for instance, during sleeping. The cervical spine part 54 comprises a posterior neck retainer 62 positioned so as to abut against the patient's posterior neck at a height somewhat lower than the cheek rest 65 and a posterior neck retainer belt 63 for mounting the posterior neck retainer 62. It will be apparent that the posterior neck retainer 62 and the posterior neck retainer belt 63 are made of soft material (for instance, soft vinyl chloride) that provides no troubles and gives no uncomfortable feeling when in direct contact with the patient's skin, as well as that appropriate shock absorbing sponge pieces or the likes may be appended to the neck retainer. It is also designed such that the posterior neck retainer belt 63 can be overlapped to fix for supporting the cervical spine in the case when the posterior neck retainer 62 is removed. The neck retainer 62 is not used simultaneously with a temple—occiput rest 55 shown in FIG. 29. In the front surface of the chest part 51 are mounted receptacles for shoulder belts 57 at the upper right and left portions and receptacles for belly belts 58 at the right and left lower portions thereof, by which a patient can put the belts with ease by himself. A cervical spine fixture 59 is disposed near the center in the front surface of the chest part 51. A pair of anti falling members 61 are rotatably mounted to the right and left portions above the cervical spine fixture 59. The cervical spine fixture 59 has an upper half whose transverse cross sectional shape is generally equal to that of a cervical spine support beam 60 and a lower half in a plate-like shape. The plate-like part is rivetted to the chest part 51. Thus, the height for a cervical spine part 64 is determined by enhousing the bottom portion of the cervical spine support beam 60 into a groove defined with the upper half of the cervical spine fixture 59 and the chest part 51.

It is also possible to bulge similar fence members as the extension of the chest part instead of the cervical spine part to both lower jaw portions to thereby suppress the mobility of the cervical spine. Since both of the fence members are extended to lower jaw—cheek parts, the mobility in all of the directions (that is, forward flexion, backward flexion, lateral flexions and rotation of the cervical spine) can be inhibited in combination with the mounting of the temple—occiput rest. Forward turning of the entire cervical spine part 54 can be prevented by securing the intermediate part of the cervical spine support beam 60 by the anti-falling members 61 as shown in the drawing. Upon use, the anti-falling members 61 are turned to their horizontal positions after the setting of the cervical spine support beam 60, and each of the inner ends of the anti-falling members 61 is secured to the chest part 51 by threading engagement or a similar way. The cervical spine fixture 59 and the anti-falling members 61 are made of appropriate metal or plastic. As shown in FIG. 28, the lumbar spine part 53 is applied and clamped to the patient's waist by means of lumbar belts 70.

Explanation will next be made specifically to the structure of the back part 52 and the lumbar spine part 53, as well as the connection between them together with the structure for the temple—occiput rest 55 in the embodiment according to this invention referring to FIG. 29.

As described above, the metal support plate 73 is fixed to the back part 52 along the back bone, and a lumbar support beam 56 is secured at the center of the lumbar spine part 53. A pair of sub-support beams 71 made of metal are secured vertically to the right and left positions of the lumbar spine part 53, for instance, by rivetting. The lumbar support beam 56 is adjustably secured by threading engagement of a fastening screw 68 to the metal support plate 73 formed with elongate holes. The sub-support beams 71 attached on both sides of the lumbar spine part 53 are inserted and situated at the upper ends thereof into space of the sub-support beam receptacles 72 respectively mounted on the chest part 51. The back part 52 has shoulder belt receptacles 57' and belly belt receptacles 58' at four corners thereof.

The temple—occiput rest 55 has a depending neck support beam 67, which is adjustably connected to the back part 52 by means of holes threadedly formed at the lower part of the depending neck support beam 67 and set screws 69 applied thereto.

The upper end of the temple—occiput rest 55 is formed, for instance, into a T-shaped configuration and prepared so that it can surround fixedly the occiput—temple region of the patient. A forehead retainer belt 66 appended with a fastener tape is attached to the lateral portion of the T-shaped rest.

The method of using the trunk corset according to this invention is to be described. As shown in FIG. 29, the lumbar support beam 56 and the neck support beam 67 are situated to fix at the back part by using fastening screws 68 and set screws 69 while controlling the entire length in accordance with the various conditions such as the body constitution and symptoms of a patient. Then, the assembly is fitted to a patient from behind and, as shown in FIG. 28, the lumbar belts 70 are clamped and the shoulder belts 57 and the belly belts 58 are clamped respectively to each of their receptacles 57' and □'. In this case, the length for each of the belts is adjusted so as to secure required fixing force as desired.

Referring then to the method of applying the cervical spine part 54, the posterior neck retainer belts 63 are previously separated into right and left parts. Then the open end of the cervical spine support beam 60 are moderately spreaded to the left and right by the resiliency thereof. The patient's neck is inserted through the spread opening of the neck support beam and fixed to the forward position. Then, the belts 63 situated at the posterior neck retainer patient's occiput are overlaid to join at the back surface of the posterior neck retainer 62, which is in moderately close contact with the posterior neck of the patient (not shown). The joining is made by Velcro tapes. If the posterior neck retainer 62 is no longer necessary, the posterior neck retainer belts 63 at the left and right can also be connected to fix to each other directly. The cheek rests 65 are put against the patient's cheeks to prevent the rotation, forward flexion and lateral flexions of the neck. It is also possible to increase or decrease the fixing force by adjusting the angle and the distance between the face and the cheek rests. The temple—occiput rest 55 is fixed at the back part 52 while adjusting the height of the neck support beam 67 to an appropriate level corresponding to the patient's occiput.

The trunk corset according to this invention is assembled and used as described above. The chest part, back part, lumbar part and neck are manufactured by previously preparing their plaster models corresponding to the body configuration of a patient and conforming various parts on the model. Upon using the corset, the best fixation can be attained by adjusting the fastening position for each of the fastener tapes. It is also possible to slacken or detach a desired part or parts depending on the various conditions of the patient such as sleeping, moving, walking, taking meals and rest, as well as relieve of the symptoms.

What is claimed is:

1. A cervical spine corset which comprises:
   (a) a cheek rest part adapted to be abutted against a cheek of a patient;
   (b) an upper chest contact part; and
   (c) a posterior neck part adapted to be abutted against the posterior neck of the patient lower than the occipital node of the patient;
   (d) said cheek rest part and said upper rest contact part being capable of being manually adjustably bent into a desired shape and having recovering resiliency;
   (e) said upper chest contact part comprising a U-shaped portion which has a U-shaped configuration when viewed from above, first turning portions integrally turning from the two upper ends of said U-shaped portion generally perpendicularly thereto, and second turning portions integrally turning from each of said first turning portions generally perpendicularly thereto, said first turning portions forming belt attaching portions to which said posterior neck rest part is adjustably attached during use;
   (f) the relative positions between said cheek rest part and said posterior neck rest part being adjustable;
   (g) the two free ends of said second turning portions being spaced from each other so that the patient can open his or her mouth freely; and
   (h) said U-shaped portion and said first and second turning portions being formed integrally.

2. A cervical spine corset according to claim 1 comprising two cheek rest parts, one adapted to be abutted against each cheek of the patient.

3. A cervical spine corset according to claim 1 in which said upper cheek contact part is formed from a metal wire of about 3 mm to 10 mm in diameter.

4. A cervical spine corset which comprises:
   (a) a wide main body which, in use, is mounted on both shoulders of a patient, said wide main body having a back part adapted to be abutted against the upper back of the patient;
   (b) a chest part attached to the front end of said wide main body so as to abut against the chest of the patient;
   (c) an occiput rest attached to the back part of said wide main body so as to abut against the posterior neck of the patient lower than the occipital node of the patient;
   (d) a pair of cheek rests adapted to be abutted independently against the cheeks of the patient without being in contact with each other, there being a space facing the front part of the patient's jaw and mouth;
   (e) said pair of cheek rests and said occiput rest being respectively connected to an intermediate portion of said wide main body and to the back part of said wide main body by means of a cheek rest support frame and an occiput rest support frame, respectively; and
   (f) said cheek rest support frame and said occiput rest support frame being formed from metal wires that can be bent into a desired shape and have recovering resiliency.

5. A cervical spine corset according to claim 4 wherein:
   (a) said wide main body is generally in a U-shaped configuration as viewed from above and is curved in an arcuate shape as viewed from the side and
   (b) a pair of belts adapted to abut against the patient's side belly are attached at the lower ends at said back part.

6. A cervical spine corset according to claim 4 wherein:
   (a) said back part is adapted to be abutted against the back of the patient;
   (b) two support frames extend upwardly from said chest part and are joined at the upper ends thereof to an upper portion of said occiput rest support frame;
   (c) said cheek rest support frame is attached to said support frames;
   (d) said chest part has detachable villi-type tape fasteners; and
   (e) said back part and said chest part are connected by means of adjustable belts.

7. A cervical spine corset which comprises:
   (a) a chest part adapted to be abutted against the chest of a patient;
   (b) a back part adapted to be abutted against the back of the patient, said back part being connected adjustably and detachably to said chest part;
   (c) a lumbar spine part adapted to be abutted against the lumbar region of the patient, said lumbar spine part being connected adjustably and detachably to said back part; and
   (d) a cervical spine part adapted to be detachably attached to an upper portion of said chest part, said cervical spine part being formed from a metal wire and bent generally in an L-shaped configuration when viewed from the side;
   (e) the upper top ends of said cervical spine part being shaped to abut against both cheeks of the patient during use by being respectively bent circularly;
   (f) cheek rests mounted on said upper top ends of said cervical spine part, said cheek rests being adapted to be abutted against the cheeks of the patient and being made of soft plastic;

(g) said cervical spine part further comprising a posterior neck retainer positioned so as to abut against the patient's posterior neck at a height somewhat lower than said cheek rests and a belt for mounting said posterior neck retainer; and (h) said cheek rests comprising a set of front parts which are connected to each other in front of the patient's mouth by means of a belt attached to the end of each part.

8. A cervical spine corset according to claim 7 wherein:

(a) said lumbar spine part comprises a support beam formed with threaded holes;

(b) said back part comprises a metal support plate formed with threaded holes; and (c) said support beam and said support plate are detachably connected to each other by means of screws.

9. A cervical spine corset which comprises:

(a) a chest part adapted to be abutted against the chest of a patient;

(b) a back part adapted to be abutted against the back of the patient, said back part being connected adjustably and detachably to said chest part;

(c) a lumbar spine part adapted to be abutted against the lumbar region of the patient, said lumbar spine part being connected adjustably and detachably to said back part; and (d) a temple—occiput rest part detachably and adjustably attached to said back part;

(e) said temple-occiput rest part comprising a temple-occiput rest, a neck support beam adjustably connected to said back part by means of holes threadedly formed in the lower part of said neck support beam and a set screw threadedly received in one of said holes, and a forhead retainer belt attached to the lateral portion of said temple—occiput rest with fastener tape; and (f) the upper end of said temple-occiput rest being formed into a T-shaped configuration and shaped so that it fixedly surrounds the occiput temple region of the patient.

10. A cervical spine corset according to claim 9 wherein:

(a) said lumbar spine part comprises a support beam formed with threaded holes;

(b) said back part comprises a metal support plate formed with threaded holes; and (c) said support beam and said support plate are detachably connected to each other by means of screws.

* * * * *